(12) United States Patent
Sztuk et al.

(10) Patent No.: US 11,808,945 B2
(45) Date of Patent: Nov. 7, 2023

(54) EYE DATA AND OPERATION OF HEAD MOUNTED DEVICE

(71) Applicant: Meta Platforms Technologies, LLC, Menlo Park, CA (US)

(72) Inventors: Sebastian Sztuk, Menlo Park, CA (US); Salvael Ortega Estrada, Redmond, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 17/468,578

(22) Filed: Sep. 7, 2021

(65) Prior Publication Data

US 2023/0071993 A1    Mar. 9, 2023

(51) Int. Cl.

| | |
|---|---|
| G02B 27/01 | (2006.01) |
| A61B 3/11 | (2006.01) |
| A61B 3/113 | (2006.01) |
| A61B 5/024 | (2006.01) |
| G02B 27/00 | (2006.01) |
| G06F 3/16 | (2006.01) |
| G06V 40/16 | (2022.01) |
| G06V 40/18 | (2022.01) |
| H04R 1/10 | (2006.01) |

(52) U.S. Cl.
CPC .......... *G02B 27/0172* (2013.01); *A61B 3/112* (2013.01); *A61B 3/113* (2013.01); *A61B 5/02438* (2013.01); *G02B 27/0093* (2013.01); *G02B 27/0101* (2013.01); *G06F 3/165* (2013.01); *G06V 40/171* (2022.01); *G06V 40/193* (2022.01); *H04R 1/1083* (2013.01); *G02B 2027/0118* (2013.01); *G02B 2027/0138* (2013.01); *G02B 2027/0178* (2013.01)

(58) Field of Classification Search
USPC .......................................................... 345/8
See application file for complete search history.

(56) References Cited

U.S. PATENT DOCUMENTS

| | | | | |
|---|---|---|---|---|
| 2002/0044152 | A1* | 4/2002 | Abbott, III et al. | G02B 27/017 345/629 |
| 2012/0050142 | A1* | 3/2012 | Border et al. | G02B 27/0101 345/8 |
| 2013/0114043 | A1* | 5/2013 | Balan et al. | A61B 3/113 351/210 |
| 2013/0127980 | A1* | 5/2013 | Haddick et al. | G06F 3/013 348/14.08 |
| 2013/0335303 | A1* | 12/2013 | Maciocci et al. | G02B 27/017 345/8 |
| 2014/0132484 | A1* | 5/2014 | Pandey et al. | G06T 19/006 345/8 |

(Continued)

FOREIGN PATENT DOCUMENTS

WO        2017134629 A1    8/2017

OTHER PUBLICATIONS

International Search Report and Written Opinion for International Application No. PCT/US2022/042639, mailed Feb. 2, 2023, 19 pages.

(Continued)

*Primary Examiner* — Chineyere D Wills-Burns
(74) *Attorney, Agent, or Firm* — FREESTONE INTELLECTUAL PROPERTY LAW PLLC; Aaron J. Visbeek

(57) ABSTRACT

A method of operating a head mounted device includes capturing eye data with one or more sensors of the head mounted device. The one or more sensors are configured to sense an eyebox region. Operations of the head mounted device are adjusted in response to the eye data.

18 Claims, 12 Drawing Sheets

(56) References Cited

U.S. PATENT DOCUMENTS

| | | | |
|---|---|---|---|
| 2014/0184550 A1* | 7/2014 | Hennessey et al. | G06F 3/041 |
| | | | 345/173 |
| 2015/0003819 A1* | 1/2015 | Ackerman et al. | G03B 13/36 |
| | | | 396/51 |
| 2015/0253573 A1* | 9/2015 | Sako et al. | H04N 13/398 |
| | | | 345/207 |
| 2015/0341734 A1 | 11/2015 | Sherman | |
| 2016/0048220 A1* | 2/2016 | Shen | G02B 27/0172 |
| | | | 345/8 |
| 2017/0103574 A1* | 4/2017 | Faaborg et al. | G06T 19/006 |
| 2017/0245803 A1* | 8/2017 | Ahmed et al. | A61B 5/7203 |
| 2018/0003966 A1 | 1/2018 | Kilcher et al. | |
| 2018/0088323 A1* | 3/2018 | Bao et al. | G02B 27/017 |
| 2018/0113508 A1* | 4/2018 | Berkner-Cieslicki et al. | |
| | | | G02B 27/0172 |
| 2018/0180882 A1* | 6/2018 | Tuli | G02B 27/0012 |
| 2018/0292895 A1* | 10/2018 | Schluessler et al. | G06F 3/013 |
| 2020/0020162 A1* | 1/2020 | Jones et al. | G01C 21/20 |
| 2020/0058256 A1 | 2/2020 | Seibert et al. | |
| 2020/0111258 A1 | 4/2020 | Sears et al. | |
| 2020/0296521 A1 | 9/2020 | Wexler et al. | |
| 2020/0409455 A1* | 12/2020 | Wilson et al. | G02B 27/017 |
| 2021/0041692 A1 | 2/2021 | Zhang et al. | |
| 2021/0173275 A1 | 6/2021 | Osterhout | |
| 2022/0028406 A1 | 1/2022 | Burmistrov et al. | |

OTHER PUBLICATIONS

Invitation to Pay Additional Fees for International Application No. PCT/US2022/042639, mailed Dec. 12, 2022, 13 pages.
Non-Final Office Action mailed Nov. 18, 2022 for U.S. Appl. No. 17/521,293, filed Nov. 8, 2021, 15 pages.

* cited by examiner

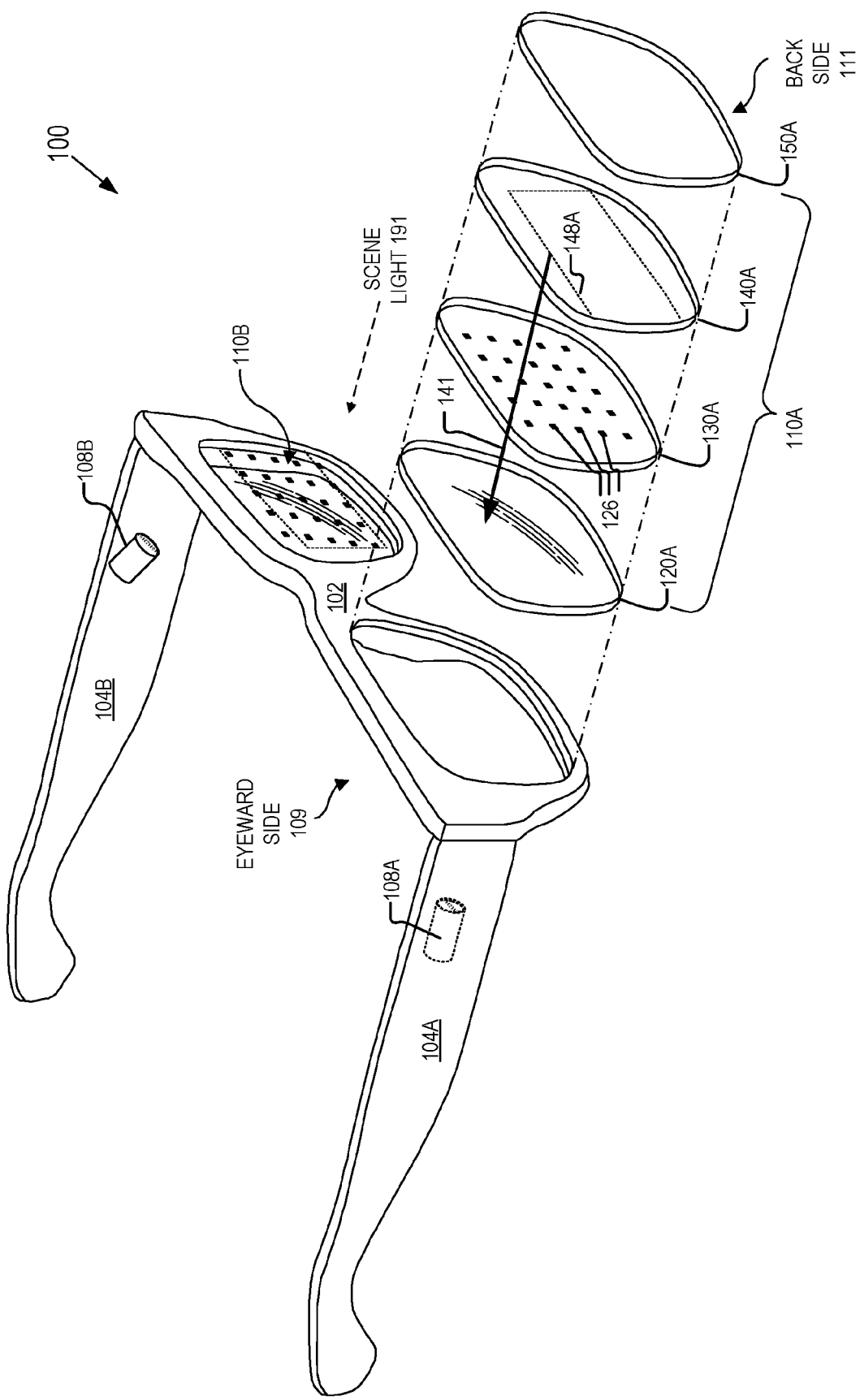

EYE DATA AND OPERATION OF HEAD MOUNTED DEVICE

TECHNICAL FIELD

This disclosure relates generally to optics, and in particular to head mounted devices.

BACKGROUND INFORMATION

A head mounted device is a wearable electronic device, typically worn on the head of a user. Head mounted devices may include one or more electronic components for use in a variety of applications, such as gaming, aviation, engineering, medicine, entertainment, activity tracking, and so on. Head mounted devices may include display to present virtual images to a wearer of the head mounted device. When a head mounted device includes a display, it may be referred to as a head mounted display. Head mounted devices may have user inputs so that a user can control one or more operations of the head mounted device.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIG. 1 illustrates an example head mounted device, in accordance with aspects of the disclosure.

DETAILED DESCRIPTION

Figure 2A:
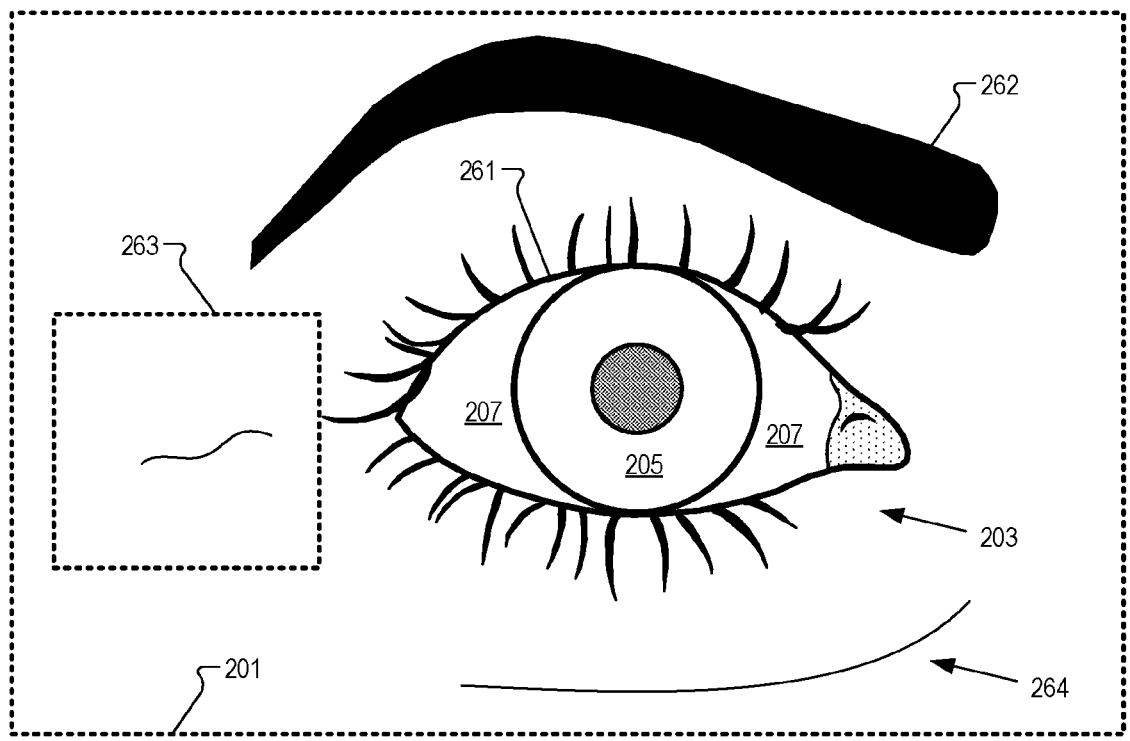
FIGS. 2A-2F illustrate various features, positions, and measurements of an eye and an eyebox region that may be included in eye data, in accordance with aspects of the disclosure.

Embodiments of operating a head mounted device in response to eye data are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some implementations of the disclosure, the term "near-eye" may be defined as including an element that is configured to be placed within 50 mm of an eye of a user while a near-eye device is being utilized. Therefore, a "near-eye optical element" or a "near-eye system" would include one or more elements configured to be placed within 50 mm of the eye of the user.

In aspects of this disclosure, visible light may be defined as having a wavelength range of approximately 380 nm – 700 nm. Non-visible light may be defined as light having wavelengths that are outside the visible light range, such as ultraviolet light and infrared light. Infrared light having a wavelength range of approximately 700 nm – 1 mm includes near-infrared light. In aspects of this disclosure, near-infrared light may be defined as having a wavelength range of approximately 700 nm - 1.6 µm.

In aspects of this disclosure, the term "transparent" may be defined as having greater than 90% transmission of light. In some aspects, the term "transparent" may be defined as a material having greater than 90% transmission of visible light.

Implementations of devices, systems, and methods of operating a head mounted device in response to eye data are disclosed herein. Eye data of a user of a head mounted device may be captured by sensors of the head mounted device. The sensors may include image sensors, photodiodes, micro-electro-mechanical systems (MEMS) mirrors, ultrasound, or LIDAR units, for example. The eye data may include one or more images of the eye, a position of the eye, a measurement of the eye (e.g. pupil size), and/or a measurement of the eye over time (e.g. speed of pupil dilation). The eye data may also include a movement of eyebrows, movement of eyelids, and/or facial micro gestures. Other examples of eye data will be disclosed in more detail below.

In an implementation of the disclosure, a transparency of a lens of a head mounted device is adjusted in response to eye data from an eyebox region of the head mounted device. By way of example, eye data may indicate that a user is squinting and a transparency of a lens of the head mounted device may be adjusted (e.g. darkened or lightened) in response to the eye data so that user is more comfortable in viewing scene light from the outside world. If the head mounted device includes a display (e.g. augmented reality head mounted display), darkening the transparency of the lens in the head mounted device may also allow the user to view virtual images generated by the display. The transparency of the lens may also be adjusted in response to an ambient light reading by a photodetector of the head mounted device. In some implementations, the transparency of the lens may be adjusted according to previously selected lens transparency settings selected by the user in similar environmental conditions (e.g. similar previous ambient light measurements). In some implementations, the transparency of the lens may be adjusted according to a predetermined lens transparency value. The predetermined lens transparency value may be derived from crowd-sourced or aggregate eye data corresponding to a particular ambient light measurement value, for example.

In an implementation of the disclosure, a display brightness of a head mounted display (e.g. augmented reality head mounted device) is adjusted in response to eye data. By way of example, eye data may indicate that a user is squinting and a display brightness of the head mounted device may be adjusted (e.g. dimmed or brightened) in response to the eye data so that user is more comfortable in viewing the display. The brightness of the display may also be adjusted in response to an ambient light reading by a photodetector of the head mounted device. In some implementations, the brightness of the display may be adjusted according to a previously selected display brightness value that was previously selected by the user in similar environmental conditions (e.g. similar previous ambient light measurements). In some implementations, the brightness of the display may be adjusted according to a predetermined display brightness value. The predetermined display brightness value may be derived from crowd-sourced or aggregate eye data corresponding to a particular ambient light measurement value, for example.

In an implementation of the disclosure, a volume of an audio output of a head mounted display (e.g. augmented reality head mounted device) is adjusted in response to eye data. By way of example, eye data may indicate that a user is uncomfortable with a particular audio output level and/or a change in an audio output level. Therefore, a volume of an audio output may be adjusted (e.g. volume up or volume down) in response to the eye data so that user is more comfortable with the audio level. The volume of the audio output may also be adjusted in response to an ambient noise measurement reading by a microphone of the head mounted device. A user comfort with a particular audio output level may depend on the noise level in a user environment. For example, the user may be comfortable with a higher audio output level in a high-noise environment (e.g. an airplane) whereas the user may be uncomfortable with the same higher audio output level in a low-noise environment (e.g. a library). These and other embodiments are described in more detail in connection with FIGS. 1-7.

FIG. 1 illustrates an example head mounted device 100, in accordance with aspects of the present disclosure. The illustrated example of head mounted device 100 is shown as including a frame 102, temple arms 104A and 104B, and near-eye optical elements 110A and 110B. Cameras 108A and 108B are shown as coupled to temple arms 104A and 104B, respectively. Cameras 108A and 108B may be configured to image an eyebox region to image the eye of the user to capture eye data of the user. Cameras 108A and 108B may image the eyebox region directly or indirectly. For example, optical elements 110A and/or 110B may have an optical combiner that is configured to redirect light from the eyebox to the cameras 108A and/or 108B. In some implementations, near-infrared light sources (e.g. LEDs or vertical-cavity side emitting lasers) illuminate the eyebox region with near-infrared illumination light and cameras 108A and/or 108B are configured to capture infrared images. Cameras 108A and/or 108B may include complementary metal-oxide semiconductor (CMOS) image sensor. A near-infrared filter that receives a narrow-band near-infrared wavelength may be placed over the image sensor so it is sensitive to the narrow-band near-infrared wavelength while rejecting visible light and wavelengths outside the narrow-band. The near-infrared light sources (not illustrated) may emit the narrow-band wavelength that is passed by the near-infrared filters.

In addition to image sensors, various other sensors of head mounted device 100 may be configured to capture eye data. Ultrasound or LIDAR chips may be configured in frame 102 to detect a position of an eye of the user by detecting the position of the cornea of the eye, for example. Discrete photodiodes included in frame 102 or optical elements 110A and/or 110B may also be used to detect a position of the eye of the user. Discrete photodiodes may be used to detect "glints" of light reflecting off of the eye, for example. Eye data generated by various sensors may not necessarily be considered "images" of the eye.

FIG. 1 also illustrates an exploded view of an example of near-eye optical element 110A. Near-eye optical element 110A is shown as including an optically transparent layer 120A, an illumination layer 130A, a display layer 140A, and a transparency modulator layer 150A. Display layer 140A may include a waveguide 148A that is configured to direct virtual images included in visible image light 141 to an eye of a user of head mounted device 100 that is in an eyebox region of head mounted device 100. In some implementations, at least a portion of the electronic display of display layer 140A is included in the frame 102 of head mounted device 100. The electronic display may include an LCD, an organic light emitting diode (OLED) display, micro-LED display, pico-projector, or liquid crystal on silicon (LCOS) display for generating the image light 141.

When head mounted device 100 includes a display, it may be considered a head mounted display. Head mounted device 100 may be considered an augmented reality (AR) head mounted display. While FIG. 1 illustrates a head mounted device 100 configured for augmented reality (AR) or mixed reality (MR) contexts, the disclosed embodiments may also be used in other implementations of a head mounted display such as virtual reality head mounted displays. Additionally, some implementations of the disclosure may be used in a head mounted device that do not include a display.

Illumination layer 130A is shown as including a plurality of in-field illuminators 126. In-field illuminators 126 are described as "in-field" because they are in a field of view (FOV) of a user of the head mounted device 100. In-field illuminators 126 may be in a same FOV that a user views a display of the head mounted device 100, in an embodiment. In-field illuminators 126 may be in a same FOV that a user views an external environment of the head mounted device 100 via scene light 191 propagating through near-eye optical elements 110. Scene light 191 is from the external environment of head mounted device 100. While in-field illuminators 126 may introduce minor occlusions into the near-eye optical element 110A, the in-field illuminators 126, as well as their corresponding electrical routing may be so small as to be unnoticeable or insignificant to a wearer of head mounted device 100. In some implementations, illuminators 126 are not in-field. Rather, illuminators 126 could be out-of-field in some implementations.

As shown in FIG. 1, frame 102 is coupled to temple arms 104A and 104B for securing the head mounted device 100 to the head of a user. Example head mounted device 100 may also include supporting hardware incorporated into the frame 102 and/or temple arms 104A and 104B. The hardware of head mounted device 100 may include any of processing logic, wired and/or wireless data interface for sending and receiving data, graphic processors, and one or more memories for storing data and computer-executable instructions. In one example, head mounted device 100 may be configured to receive wired power and/or may be configured to be powered by one or more batteries. In addition, head mounted device 100 may be configured to receive wired and/or wireless data including video data.

FIG. 1 illustrates near-eye optical elements 110A and 110B that are configured to be mounted to the frame 102. In some examples, near-eye optical elements 110A and 110B may appear transparent or semi-transparent to the user to facilitate augmented reality or mixed reality such that the user can view visible scene light from the environment while also receiving image light 141 directed to their eye(s) by way of display layer 140A. In further examples, some or all of near-eye optical elements 110A and 110B may be incorporated into a virtual reality headset where the transparent nature of the near-eye optical elements 110A and 110B allows the user to view an electronic display (e.g., a liquid crystal display (LCD), an organic light emitting diode (OLED) display, or micro-LED display, etc.) incorporated in the virtual reality headset.

As shown in FIG. 1, illumination layer 130A includes a plurality of in-field illuminators 126. Each in-field illuminator 126 may be disposed on a transparent substrate and may be configured to emit light to an eyebox region on an eyeward side 109 of the near-eye optical element 110A. In some aspects of the disclosure, the in-field illuminators 126 are configured to emit near infrared light (e.g. 750 nm - 1.6 μm). Each in-field illuminator 126 may be a micro light emitting diode (micro-LED), an edge emitting LED, a vertical cavity surface emitting laser (VCSEL) diode, or a Superluminescent diode (SLED).

Optically transparent layer 120A is shown as being disposed between the illumination layer 130A and the eyeward side 109 of the near-eye optical element 110A. The optically transparent layer 120A may receive the infrared illumination light emitted by the illumination layer 130A and pass the infrared illumination light to illuminate the eye of the user. As mentioned above, the optically transparent layer 120A may also be transparent to visible light, such as scene light 191 received from the environment and/or image light 141 received from the display layer 140A. In some examples, the optically transparent layer 120A has a curvature for focusing light (e.g., display light and/or scene light) to the eye of the user. Thus, the optically transparent layer 120A, in some examples, may be referred to as a lens. In some aspects, the optically transparent layer 120A has a thickness and/or curvature that corresponds to the specifications of a user. In other words, the optically transparent layer 120A may be a prescription lens. However, in other examples, the optically transparent layer 120A may be a non-prescription lens.

Figure 2B:
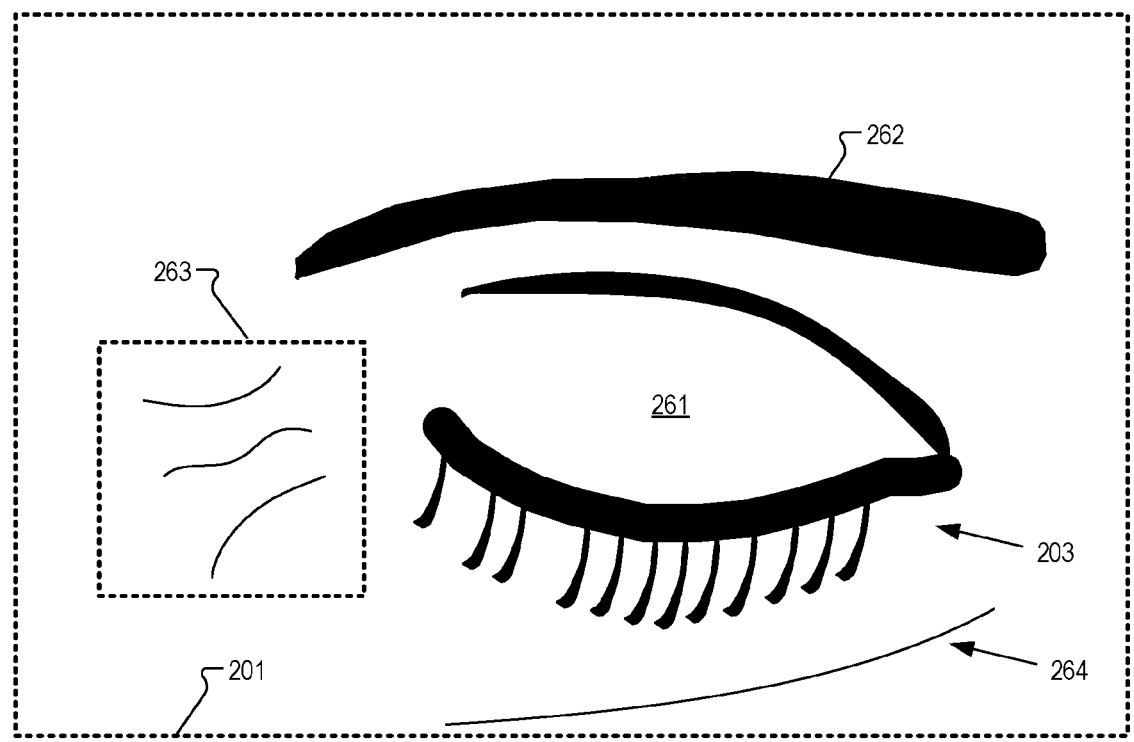

FIGS. 2A and 2B illustrate an eye 203 in an eyebox region 201, in accordance with implementations of the disclosure. FIG. 2A illustrates eye 203 that is open and FIG. 2B illustrates eye 203 shut. Eye data of eye 203 may include a position of eye 203, a measurement of the eye 203 (e.g. pupil size), and/or a measurement of the eye over time (e.g. speed of pupil dilation). The eye data may also include a movement and/or shape of eyebrows 262, movement and/or shape of eyelid 261, and/or facial micro gestures associated with skin lines for example. Eye 203 may be wide open, shut, or any variation in between. In some contexts, eye 203 may be squinting.

In FIG. 2A, most of the iris 205 and large portions of the sclera 207 are visible. When eye 203 is squinting, less of iris 205 and sclera 207 will be visible. In FIG. 2B, neither iris 205 nor sclera 207 are visible. In FIG. 2A, eyebrow 262 is arched. In FIG. 2B, eyebrow 262 is flattened and closer to eye 203 than in FIG. 2A. Similarly, smile line 264 is flattened in FIG. 2B compared to the more arched smile line 264 in FIG. 2A. FIG. 2B also illustrates an increased number of lines in corner region 263 compared to the lines in corner region 263. The shape and or number of lines in corner region 263 may correspond to micro gestures, squinting, cringing, eye strain, and/or user discomfort, for example. Therefore, detecting the size, shape, or quantity of various eye features in eyebox region 201 provides eye data that can be indicative of a user reaction or adaptation to a particular environmental context.

Figure 2C:
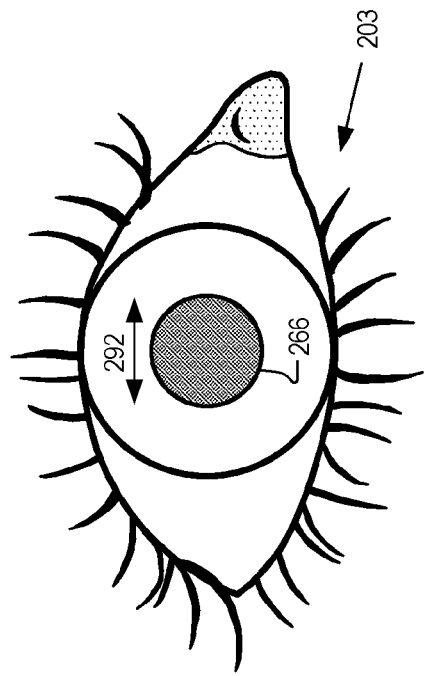

FIG. 2C illustrates eye 203 having a pupil 266 with a diameter of dimension 291. FIG. 2D illustrates eye 203 having a pupil 266 with a diameter of dimension 292 that is larger than dimension 291. In some implementations of the disclosure, eye data may include the size (e.g. diameter) of pupil 266. In some implementations of the disclosure, eye data may include the size (e.g. diameter) of pupil 266 over a particular time period. Thus, when the size of pupil 266 is captured over a plurality of time periods, the speed of pupil dilation may be determined.

Figure 2E:
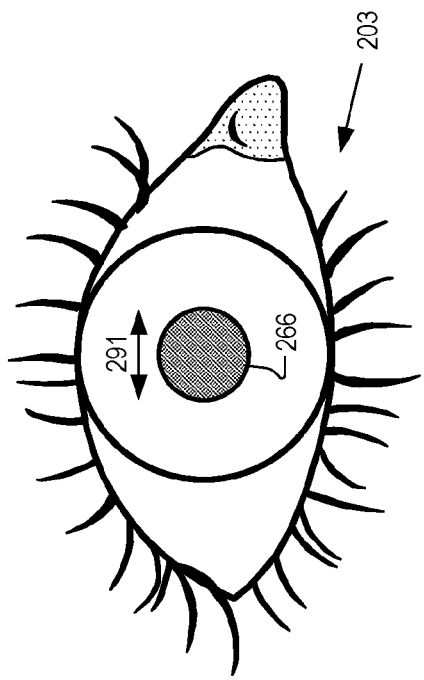
Figure 2D:
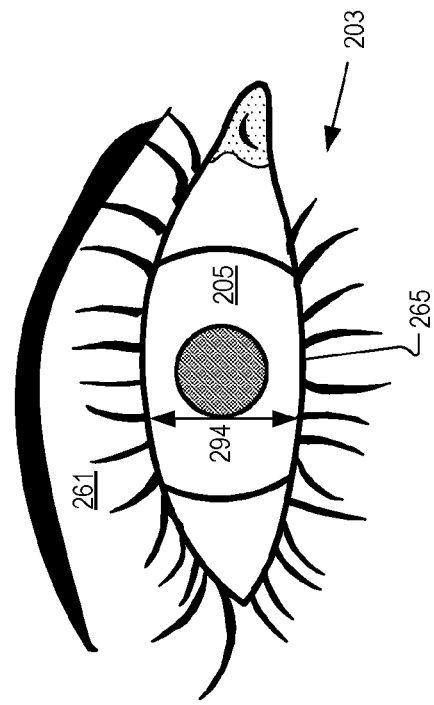
Figure 2F:
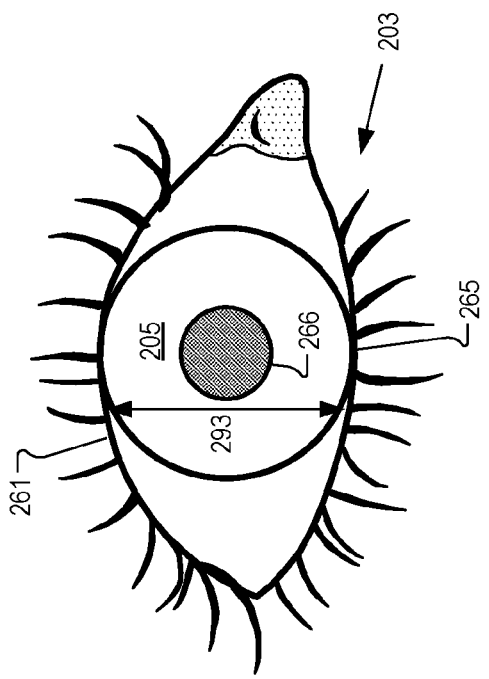

FIGS. 2E and 2F illustrate another example measurement of eye 203 that may be included in eye data, in accordance with implementations of the disclosure. For example, the dimension 293 of iris 205 between top eyelid 261 and bottom eye lid 265 is larger in FIG. 2E when compared to the dimension 294 of iris 205 when eye 203 is squinting in FIG. 2F.

Figure 3A:
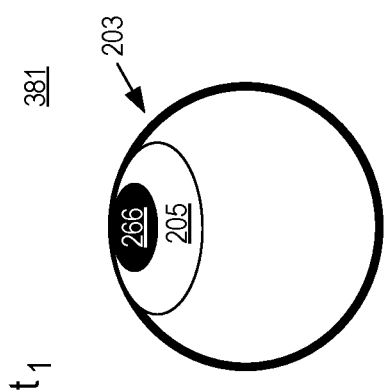
FIGS. 3A-3C illustrate various positions and measurements of an eye that may be included in eye data, in accordance with aspects of the disclosure.
Figure 3B:
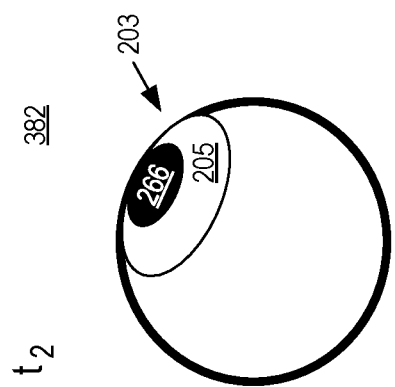
Figure 3C:
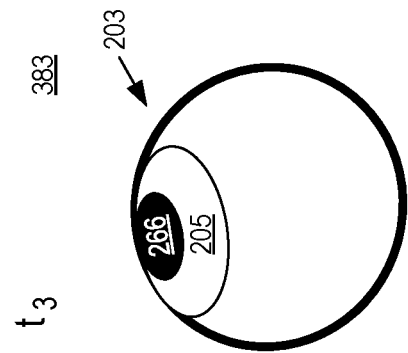

FIGS. 3A-3C illustrates different positions of eye 203 at different times, in accordance with implementations of the disclosure. FIG. 3A illustrates eye 203 in a centered position 381 at a time $t_1$. Centered position 381 may be associated with eye 203 looking straight forward at an object in the far field (e.g. focus distance of infinity). FIG. 3B illustrates eye 203 in a right-of-center position 382 at a time $t_2$. FIG. 3C illustrates eye 203 in a slightly-left-of-center position 383 at a time $t_3$. The position of eye 203 may be determined by tracking the position of pupil 266, iris 205, tracking the cornea (not specifically illustrated), and/or other suitable eye-tracking techniques. Thus, eye data may include a position of eye 203 and/or positions of eye 203 over time. The speed of a position change of eye 203 may be included in eye data. For example, if eye 203 goes from position 381 to position 382 very quickly (e.g. within 200 ms), this movement may be considered a saccade. Smaller movements of eye 203 in short time periods may be considered micro-saccades. The number of saccades or micro-saccades in a particular time period may be counted using image processing techniques or other suitable pupil position techniques. The number of saccades or micro-saccades in a particular time period may be included in eye data, in various implementations of the disclosure. The position changes of eye 203 may be considered gaze flickering where eye 203 changes position often but does not change position rapidly enough to be considered a saccade or micro-saccade. Gaze flickering may be a sign of discomfort due to ambient light brightness or display brightness.

Figure 4:
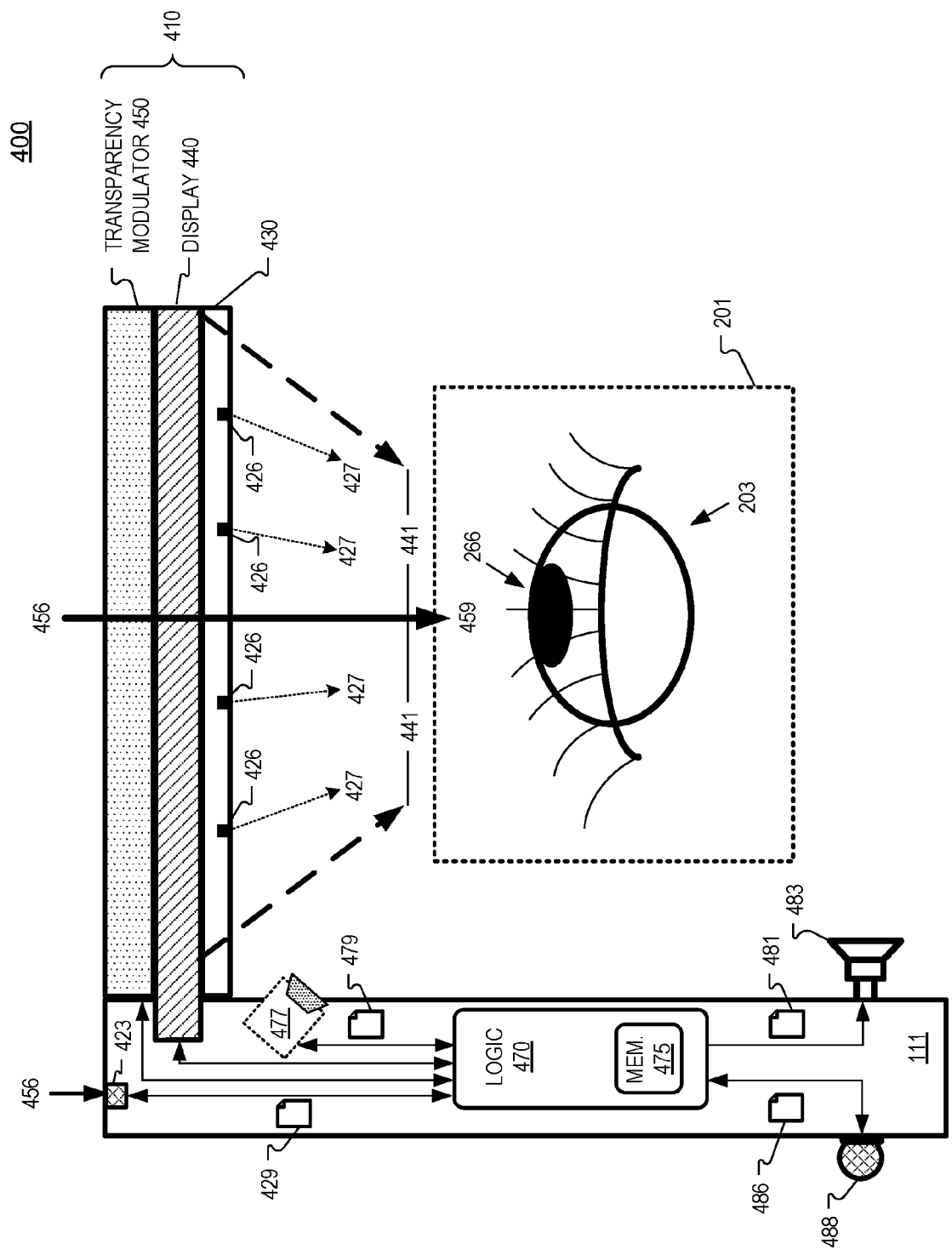
FIG. 4 illustrates a top view of a portion of an example head mounted device, in accordance with aspects of the disclosure.

FIG. 4 illustrates a top view of a portion of an example head mounted device 400, in accordance with implementations of the disclosure. Head mounted device 400 may include an optical element 410 that includes a transparency modulator layer 450, a display layer 440, and an illumination layer 430. Additional optical layers (not specifically illustrated) may also be included in example optical element 410. For example, a focusing lens layer may optionally be included in optical element 410 to focus scene light 456 and/or virtual images included in image light 441 generated by display layer 440. Transparency modulator layer 450 modulates the intensity of incoming scene light 456 so that the scene light 459 that propagates to eyebox region 201 may have a reduced intensity when compared to the intensity of incoming scene light 456.

Display layer 440 presents virtual images in image light 441 to an eyebox region 201 for viewing by an eye 203. Processing logic 470 is configured to drive virtual images onto display layer 440 to present image light 441 to eyebox region 201. Processing logic 470 is also configured to adjust a brightness of display layer 440. In some implementations, adjusting a display brightness of display layer 440 includes adjusting the intensity of one or more light sources of display layer 440. All or a portion of display layer 440 may be transparent or semi-transparent to allow scene light 456 from an external environment to become incident on eye 203 so that a user can view their external environment in addition to viewing virtual images presented in image light 441.

Transparency modulator layer 450 may be configured to change its transparency to modulate the intensity of scene light 456 that propagates to the eye 203 of a user. Processing logic 470 may be configured to drive an analog or digital signal onto transparency modulator layer 450 in order to modulate the transparency of transparency modulator layer 450. In an example implementation, transparency modulator layer 450 includes liquid crystals where the alignment of the liquid crystals is adjusted in response to a drive signal from processing logic 470 to modulate the transparency of transparency modulator layer 450. Other suitable technologies that allow for electronically controlled dimming of transparency modulator 450 may be included in transparency modulator 450.

Illumination layer 430 includes light sources 426 configured to illuminate an eyebox region 201 with infrared illumination light 427. Illumination layer 430 may include a transparent refractive material that functions as a substrate for light sources 426. Infrared illumination light 427 may be near-infrared illumination light. Camera 477 is configured to image (directly) eye 203, in the illustrated example of FIG. 4. In other implementations, camera 447 may (indirectly) image eye 203 by receiving reflected infrared illumination light from an optical combiner layer (not illustrated) included in optical element 410. The optical combiner layer may be configured to receive reflected infrared illumination light (the infrared illumination light 427 reflected from eyebox region 201) and redirect the reflected infrared illumination light to camera 447. In this implementation, camera 447 would be oriented to receive the reflected infrared illumination light from the optical combiner layer of optical element 410.

Camera 447 may include a complementary metal-oxide semiconductor (CMOS) image sensor, in some implementations. An infrared filter that receives a narrow-band infrared wavelength may be placed over the image sensor so it is sensitive to the narrow-band infrared wavelength while rejecting visible light and wavelengths outside the narrow-band. Infrared light sources (e.g. light sources 426) such as infrared LEDs or infrared VCSELS that emit the narrow-band wavelength may be oriented to illuminate eye 203 with the narrow-band infrared wavelength. Camera 447 may capture eye-tracking images of eyebox region 201. Eyebox region 201 may include eye 203 as well as surrounding features in an ocular area such as eyebrows, eyelids, eye lines, etc. Processing logic 470 may initiate one or more image captures with camera 477 and camera 477 may provide eye-tracking images 479 to processing logic 470.

Processing logic 470 may perform image processing to determine the size and/or position of various features of the eyebox region 201. For example, processing logic 470 may be configured to determine size and/or position of the features described in association with FIGS. 2A-3C. For example, processing logic 470 may perform image processing to determine a pupil position or pupil size of pupil 266. Light sources 426 and camera 477 are merely an example eye-tracking configuration and other suitable eye-tracking systems and techniques may also be used to capture eye data, in implementations of the disclosure. In an implementation, a MEMS mirror-based RGB laser system is used for capturing eye data.

In the illustrated implementation of FIG. 4, a memory 475 is included in processing logic 470. In other implementations, memory 475 may be external to processing logic 470. In some implementations, memory 475 is located remotely from processing logic 470. In implementations, virtual image(s) are provided to processing logic 470 for presentation in image light 441. In some implementations, virtual images are stored in memory 475. Processing logic 470 may be configured to receive virtual images from a local memory or the virtual images may be wirelessly transmitted to the head mounted device 400 and received by a wireless interface (not illustrated) of the head mounted device.

FIG. 4 illustrates that processing logic 470 is communicatively coupled to ambient light sensor 423. Processing logic 470 may be communicatively coupled to a plurality of ambient light sensors, in some implementations. Ambient light sensor 423 may include one or more photodetectors (e.g. photodiodes). Ambient light sensor 423 may include more than one photodetector with corresponding filters so that ambient light sensor 423 can measure the color as well as the intensity of scene light 456. Ambient light sensor 423 may include a red-green-blue (RGB)/infrared/monochrome camera sensor to generate high certainty measurements about the state of the ambient light environment. In some implementations, a world-facing image sensor of head mounted device 400 that is oriented to receive scene light 456 may function as an ambient light sensor. Ambient light sensor 423 is configured to generate an ambient light measurement 429. In the illustrated implementation, processing logic 470 is configured to receive ambient light measurement 429 from ambient light sensor 423. Processing logic 470 may also be communicatively coupled to ambient light sensor 423 to initiate the ambient light measurement.

Processing logic 470 is communicatively coupled to microphone 488 of head mounted device 400, in the example implementation of FIG. 4. Processing logic 470 may be communicatively coupled to a plurality of microphones, in some implementations. Processing logic 470 may be configured to initiate an ambient noise measurement with microphone 488. Processing logic 470 is configured to receive ambient noise measurement 486 generated by microphone 488, in FIG. 4. Ambient noise measurement 486 may be an analog or digital output of microphone 488 that is representative of the noise-level of the external environment of the head mounted device. Processing logic 470 is also configured to adjust a volume 481 of an audio output 483 of head mounted device 400. The audio output 483 may be an actual physical speaker or a wired or wireless output that drives auxiliary headphones.

In operation, transparency modulator layer 450 may be driven to various transparency values by processing logic 470 in response to various eye data and ambient light measurements 429. By way of example, a pupil diameter of an eye may indicate that scene light 456 is brighter than the user prefers. Other measurements of an ocular region (e.g. dimension of eyelids, sclera, number of lines in corner region 263, etc.) of the user may indicate the user is squinting and that scene light 456 may be brighter than the user prefers. Thus, a transparency of transparency modulator layer 450 may be driven to a transparency that makes the user more comfortable with the intensity of scene light 459 that propagates through transparency modulator layer 450. The transparency of transparency modulator layer 450 may be modulated to various levels between 10% transparent and 90% transparent, in response to the eye data and the ambient light measurement, for example.

Figure 5A:
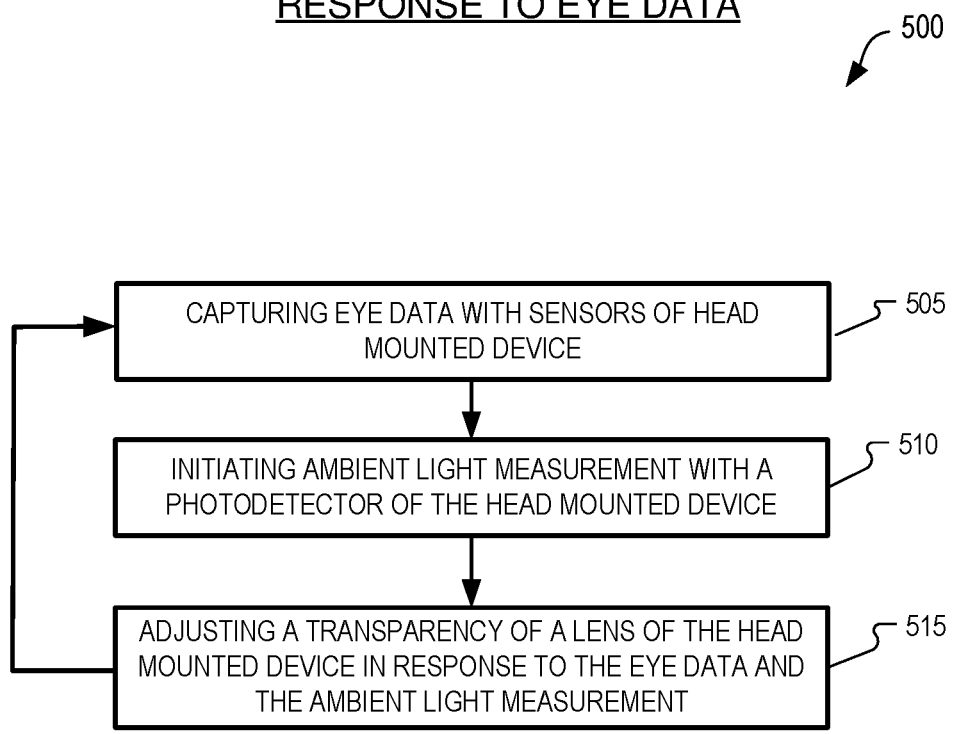
FIG. 5A illustrates a flow chart of an example method of adjusting a transparency of a lens of a head mounted device, in accordance with aspects of the disclosure.

FIG. 5A illustrates an example method of adjusting a transparency of a lens of a head mounted device, in accordance with implementations of the disclosure. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel. In some implementations, processing logic 470 executes all or a portion of process 500.

In process block 505, eye data is captured with one or more sensors of a head mounted device. The one or more sensors are configured to sense the eyebox region. The sensors may include one or more photodiodes, image sensors, or any other suitable sensor to capture eye data. As described previously, the eye data may include images of an eyebox region for example. The eye data may include positions of various features of an ocular area of a user in the eyebox region.

In process block 510, an ambient light measurement is initiated with a photodetector (e.g. ambient light sensor 423) of the head mounted device. The ambient light measurement (e.g. ambient light measurement 429) may be initiated during a same time period as the eye data is captured.

In process block 515, a transparency of a lens of the head mounted device is adjusted in response to the eye data and the ambient light measurement. The "lens" of a head mounted device may be an optical element (e.g. optical element 110 or 410) that the user views the world through. In other words, scene light (e.g. scene light 456) from an external environment of the head mounted device may propagate through the lens prior to becoming incident on an eye 203. In the illustration of FIG. 4, a transparency of transparency modulator layer 450 may be adjusted in response to eye data and ambient light measurement 429.

In some implementations, the eye data includes at least one of a pupil size of an eye, speed of pupil dilation of the eye, a gaze direction of the eye, or eye-movement data (e.g. number of saccades in a given time period).

Eye data may include one or more images (e.g. image(s) 479) of eye 203 or the ocular region of a user that occupies eyebox region 201, for example. In an implementation, process 500 further includes performing image processing on the one or more images of the eye to determine a heart rate of a user of the head mounted device. The heart rate of the user may be determined by pupil size over a time period, for example. Adjusting the transparency of the lens may be based at least in part on the heart rate of the user.

In an implementation, process 500 further includes performing image processing on the one or more images of the eye to determine at least one of movement of eyebrows, movement of eyelids, or facial muscle micro gestures. Adjusting the transparency of the lens may be based at least in part on the movement of eyebrows, movement of eyelids, and/or facial muscle micro gestures.

In an implementation of process 500, adjusting the transparency of the lens of the head mounted device in response to the eye data and the ambient light measurement includes associating the eye data and the ambient light measurement to previous eye data paired with a previous ambient light measurement and adjusting the transparency of the lens to a previously selected lens transparency selected by the user. The previously selected lens transparency corresponds to the previous eye data paired with the previous ambient light measurement. The previous eye data and the previous ambient light measurement were captured by the head mounted device during a same time period. In this way, previous transparency selections of the user can be driven onto transparency modulator layer 450 to drive the transparency of optical element 410 to be personalized to previous selections of the user.

Figure 5B:
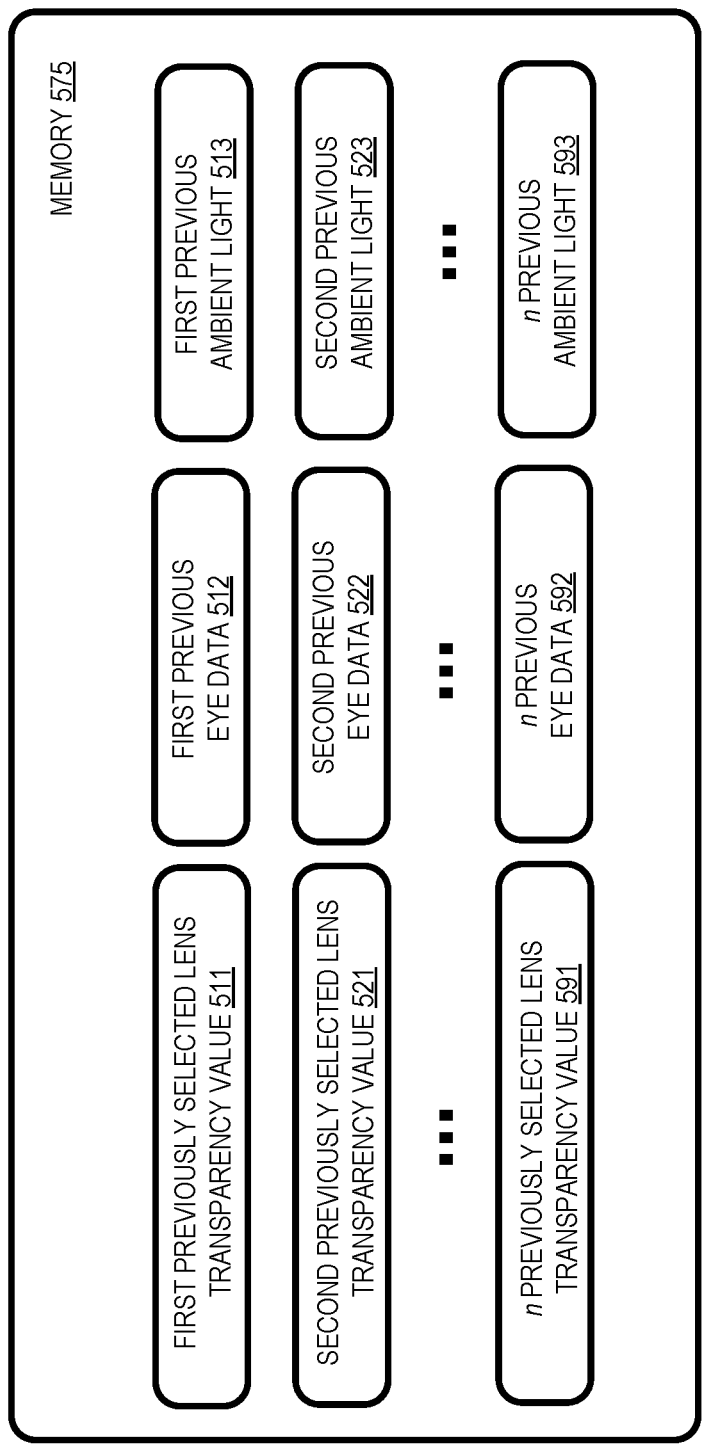
FIGS. 5B-5C illustrates example memories that may be implemented in a method of adjusting a transparency of a lens of a head mounted device, in accordance with aspects of the disclosure.

To illustrate, FIG. 5B illustrates example previous eye data paired with previous ambient light measurements in a memory 575, in accordance with implementations of the disclosure. Memory 575 may be included in memory 475, for example.

In FIG. 5B, previous eye data is paired with previous ambient light measurements and previously selected lens transparency values correspond to the previous ambient light measurements paired with the previous eye data. Therefore, memory 575 includes the transparency values a user selected in various ambient light environments where certain eye data was also present. For example, first previous eye data 512 is paired with first previous ambient light measurement 513. First previously selected lens transparency value 511 corresponds with the pairing of data 512 and 513. A user of a head mounted device may have previously selected first previously selected lens transparency value 511 when (or immediately after) the first previous ambient light measurement 513 and first previous eye data 512 were collected by a head mounted device.

Second previous eye data 522 is paired with second previous ambient light measurement 523. Second previously selected lens transparency value 521 corresponds with the pairing of data 522 and 523. A user of a head mounted device may have previously selected second previously selected lens transparency value 521 when (or immediately after) the second previous ambient light measurement 523 and second previous eye data 522 were collected by a head mounted device.

Memory 575 may include integer n number of previously selected lens transparency values corresponding to previous eye data paired with previous ambient light measurements. Thus, given an ambient light measurement (e.g. 429) and eye data, a personalized transparency value (previously selected by the user during similar ambient light conditions matched to similar eye data) can be driven onto transparency modulator layer 450 to adjust the intensity of scene light 459.

In an implementation of process 500, adjusting the transparency of the lens of the head mounted device in response to the eye data and the ambient light measurement includes adjusting the transparency of the lens of the head mounted device to a predetermined lens transparency value associated with aggregate eye data corresponding to the ambient light measurement. In this way, transparency selections determined in testing, crowd-sourced data or averaged from user preferences can be driven onto transparency modulator layer 450 to drive the transparency of optical element 410 to predetermined transparency values that were comfortable under similar ambient light conditions and eye data.

Figure 5C:
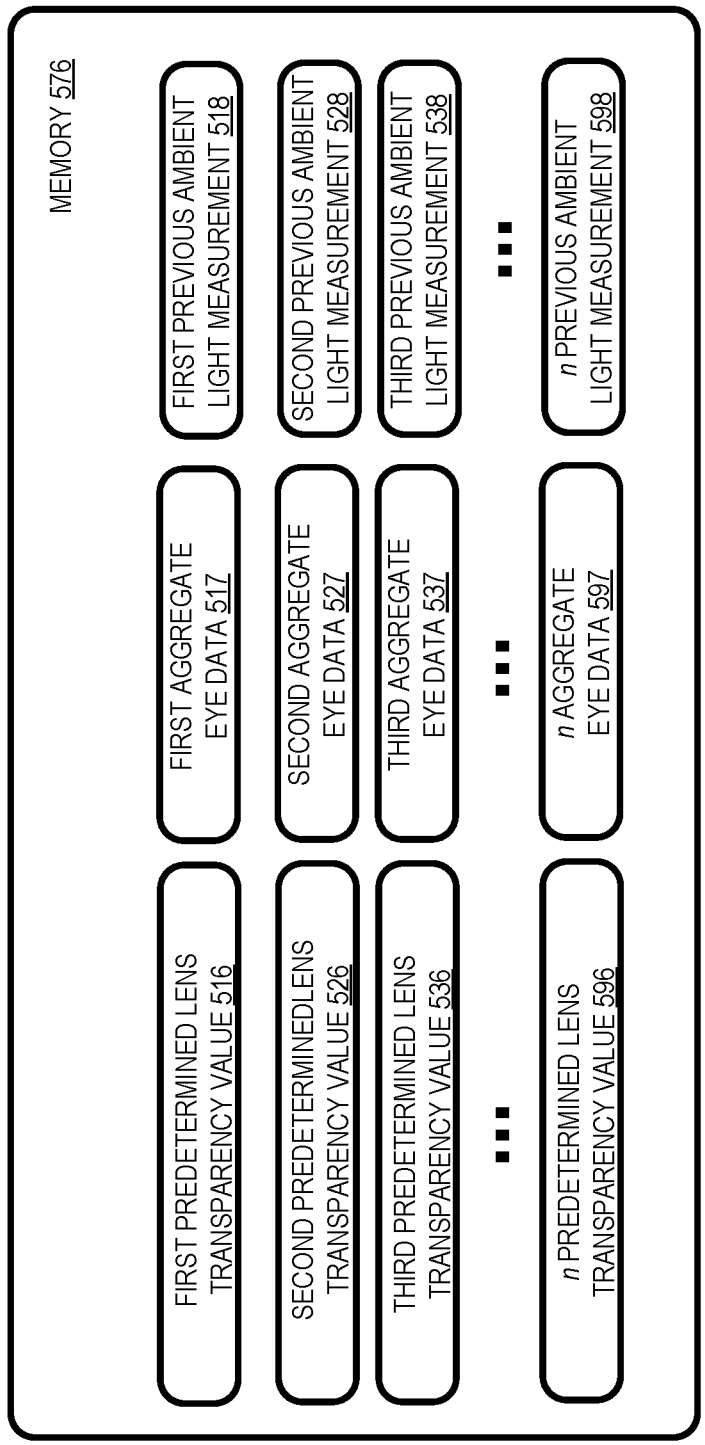

To illustrate, FIG. 5C illustrates example aggregate eye data paired with ambient light measurements in a memory 576, in accordance with implementations of the disclosure. Memory 576 may be included in memory 475, for example.

In FIG. 5C, aggregate eye data is paired with previous ambient light measurements and predetermined lens transparency values correspond to the previous ambient light measurements paired with the aggregate eye data. Therefore, memory 576 may include predetermined lens transparency values selected by the average user in various ambient light environments where certain eye data was also present. For example, first aggregate eye data 517 is paired with first previous ambient light measurement 518. First predetermined lens transparency value 516 corresponds with the pairing of data 517 and 518. An average user setting of a head mounted device may have first predetermined lens transparency value 516 when (or immediately after) the first previous ambient light measurement 518 and first aggregate eye data 517 were collected by a head mounted device.

Second aggregate eye data 527 is paired with second previous ambient light measurement 528. First predetermined lens transparency value 526 corresponds with the pairing of data 527 and 528. An average user setting of a head mounted device may have second predetermined lens transparency value 526 when (or immediately after) the second previous ambient light measurement 528 and second aggregate eye data 527 were collected by a head mounted device.

Memory 576 may include integer n number of predetermined lens transparency values corresponding to aggregate eye data paired with previous ambient light measurements. Thus, given an ambient light measurement (e.g. 429) and aggregate eye data for that particular ambient light measurement, a predetermined lens transparency value known to be suitable for the ambient light measurement and eye data can be driven onto transparency modulator layer 450 to adjust the intensity of scene light 459.

Figure 6A:
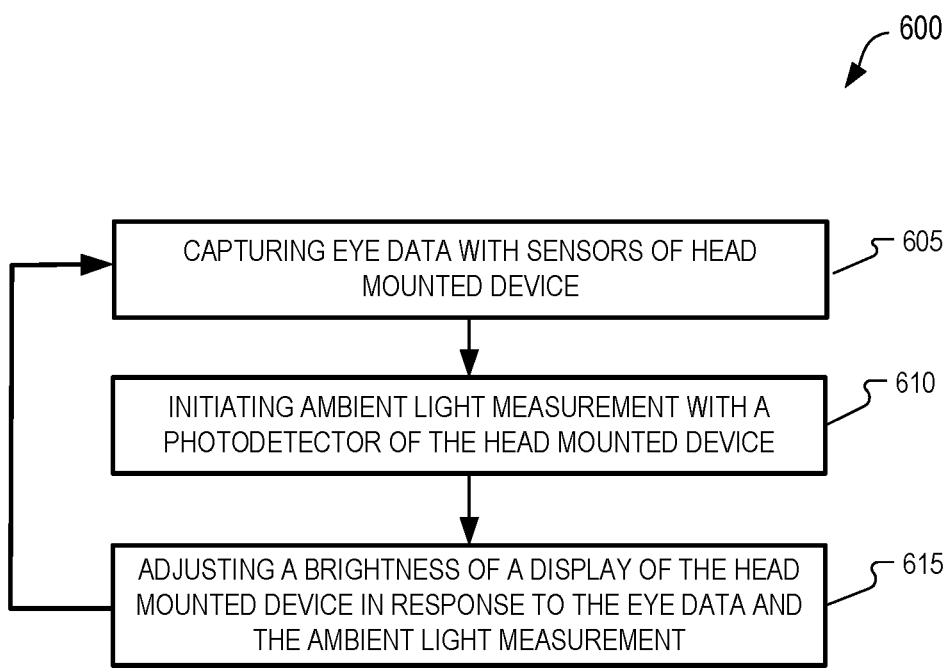
FIG. 6A illustrates a flow chart of an example method of adjusting a display brightness of a head mounted device, in accordance with aspects of the disclosure.

FIG. 6A illustrates an example method of adjusting a display brightness of head mounted device, in accordance with implementations of the disclosure. The order in which some or all of the process blocks appear in process 600 should not be deemed limiting. Rather, one of ordinary skill in the art having the benefit of the present disclosure will understand that some of the process blocks may be executed in a variety of orders not illustrated, or even in parallel. In some implementations, processing logic 470 executes all or a portion of process 600.

In process block 605, eye data is captured with one or more sensors of a head mounted device. The one or more sensors are configured to sense the eyebox region. The sensors may include one or more photodiodes, image sensors, or any other suitable sensor to capture eye data. As described previously, the eye data may include images of an eyebox region, for example. The eye data may include positions of various features of an ocular area of a user in the eyebox region.

In process block 610, an ambient light measurement is initiated with a photodetector (e.g. ambient light sensor 423) of the head mounted device. The ambient light measurement (e.g. ambient light measurement 429) may be initiated during a same time period as the eye data is captured.

In process block 615, a brightness of a display of the head mounted device is adjusted in response to the eye data and the ambient light measurement. In the illustration of FIG. 4, a brightness of display layer 440 may be adjusted in response to eye data and ambient light measurement 429.

In some implementations, the eye data includes at least one of a pupil size of an eye, speed of pupil dilation of the eye, a gaze direction of the eye, or eye-movement data (e.g. number of saccades in a given time period).

Eye data may include one or more images (e.g. image(s) 479) of eye 203 or the ocular region of a user that occupies eyebox region 201, for example. In an implementation, process 600 further includes performing image processing on the one or more images of the eye to determine a heart rate of a user of the head mounted device. The heart rate of the user may be determined by pupil size over a time period, for example. Adjusting the brightness of the display may be based at least in part on the heart rate of the user.

In an implementation, process 600 further includes performing image processing on the one or more images of the eye to determine at least one of movement of eyebrows, movement of eyelids, or facial muscle micro gestures. Adjusting the brightness of the display may be based at least in part on the movement of eyebrows, movement of eyelids, and/or facial muscle micro gestures.

In an implementation of process 600, adjusting the brightness of the display in response to the eye data and the ambient light measurement includes associating the eye data and the ambient light measurement to previous eye data paired with a previous ambient light measurement and adjusting the brightness of the display to a previously selected display brightness selected by the user. The previously selected display brightness corresponds to the previous eye data paired with the previous ambient light measurement and the previous eye data and the previous ambient light measurement were captured by the head mounted device during a same time period. In this way, previous display brightness selections of the user can be driven onto display layer 440 to drive the brightness of the display to be personalized to previous selections of the user.

Figure 6B:
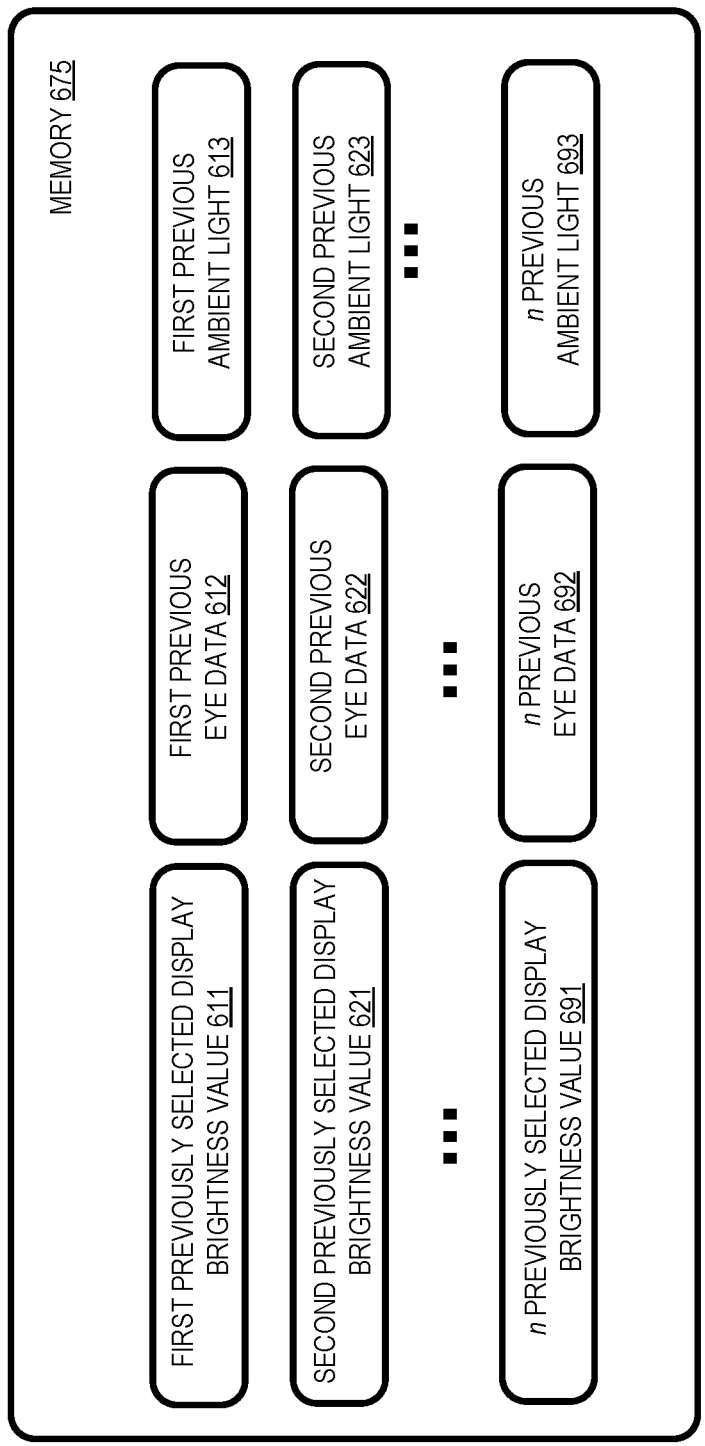
FIGS. 6B-6C illustrates example memories that may be implemented in a method of adjusting a display brightness of a head mounted device, in accordance with aspects of the disclosure.

To illustrate, FIG. 6B illustrates example previous eye data paired with previous ambient light measurements in a memory 675, in accordance with implementations of the disclosure. Memory 675 may be included in memory 475, for example.

In FIG. 6B, previous eye data is paired with previous ambient light measurements and previously selected display brightness values correspond to the previous ambient light measurements paired with the previous eye data. Therefore, memory 675 includes the brightness values a user selected in various ambient light environments where certain eye data was also present. For example, first previous eye data 612 is paired with first previous ambient light measurement 613. First previously selected display brightness value 611 corresponds with the pairing of data 612 and 613. A user of a head mounted device may have previously selected first previously selected display brightness value 611 when (or immediately after) the first previous ambient light measurement 613 and first previous eye data 612 were collected by a head mounted device.

Second previous eye data 622 is paired with second previous ambient light measurement 623. Second previously selected display brightness value 621 corresponds with the pairing of data 622 and 623. A user of a head mounted device may have previously selected second previously selected display brightness value 621 when (or immediately after) the second previous ambient light measurement 623 and second previous eye data 622 were collected by a head mounted device.

Memory 675 may include integer n number of previously selected display brightness values corresponding to previous eye data paired with previous ambient light measurements. Thus, given an ambient light measurement (e.g. 429) and eye data, a personalized display brightness value (previously selected by the user during similar ambient light conditions matched to similar eye data) can be driven onto display layer 440 to adjust a brightness of image light 441.

In an implementation of process 600, adjusting the brightness of the display of the head mounted device in response to the eye data and the ambient light measurement includes adjusting the brightness of the display to a predetermined display brightness associated with aggregate eye data corresponding to the ambient light measurement. In this way, display brightness selections determined in testing, crowd-sourced data, or averaged from user preferences can be driven onto display layer 440 to drive display layer 440 to brightness levels that are comfortable under similar ambient light conditions and eye data.

Figure 6C:
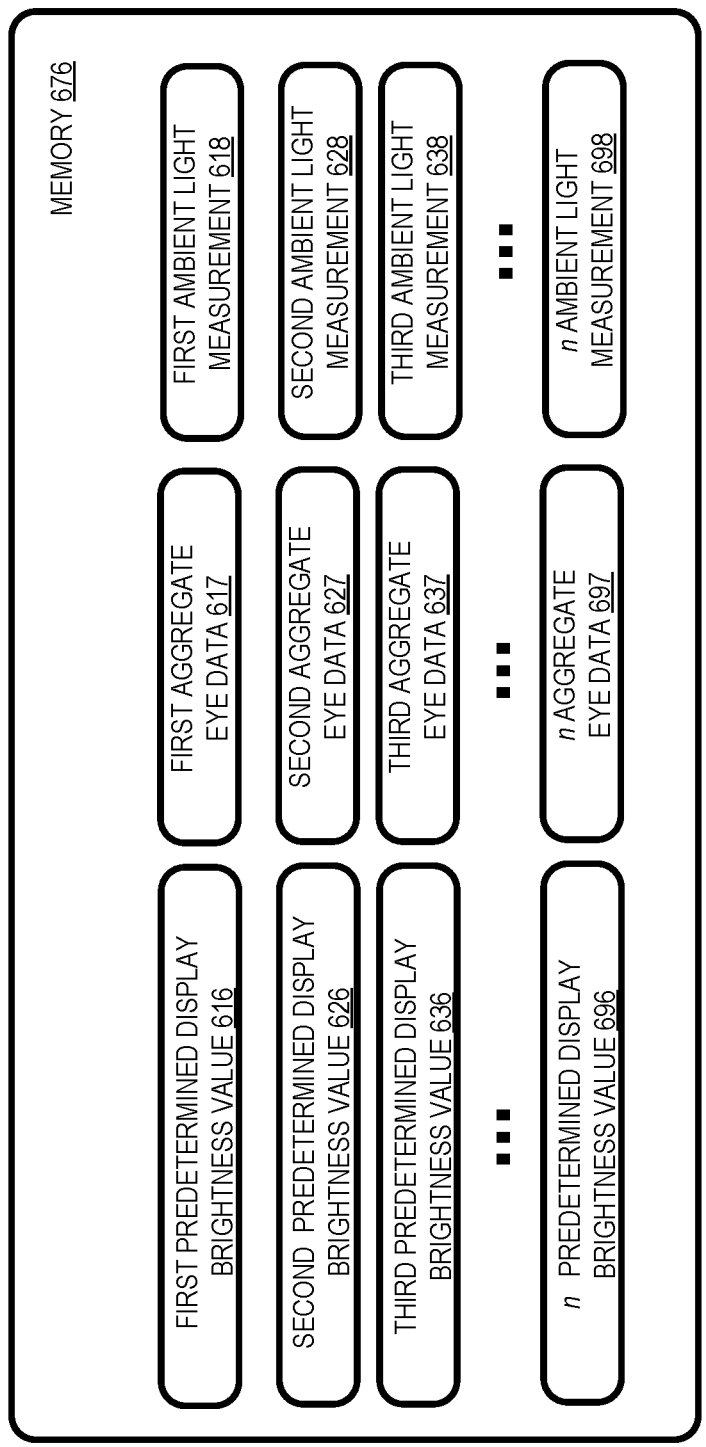

To illustrate, FIG. 6C illustrates example aggregate eye data paired with ambient light measurements in a memory 676, in accordance with implementations of the disclosure. Memory 676 may be included in memory 475, for example.

In FIG. 6C, aggregate eye data is paired with previous ambient light measurements and predetermined display brightness values correspond to the previous ambient light measurements paired with the aggregate eye data. Therefore, memory 676 may include predetermined display brightness values selected by the average user in various ambient light environments where certain eye data was also present. For example, first aggregate eye data 617 is paired with first previous ambient light measurement 618. First predetermined display brightness value 616 corresponds with the pairing of data 617 and 618. An average user setting of a head mounted device may have first predetermined display brightness value 616 when (or immediately after) the first previous ambient light measurement 618 and first aggregate eye data 617 were collected by a head mounted device.

Second aggregate eye data 627 is paired with second previous ambient light measurement 628. First predetermined display brightness value 626 corresponds with the pairing of data 627 and 628. An average user setting of a head mounted device may have second predetermined display brightness value 626 when (or immediately after) the second previous ambient light measurement 628 and second aggregate eye data 627 were collected by a head mounted device.

Memory 676 may include integer n number of predetermined display brightness values corresponding to aggregate eye data paired with previous ambient light measurements. Thus, given an ambient light measurement (e.g. 429) and aggregate eye data for that particular ambient light measurement, a predetermined display brightness value known to be suitable for the ambient light measurement and eye data can be driven onto display layer 440 to adjust a brightness of image light 441.

Figure 7:
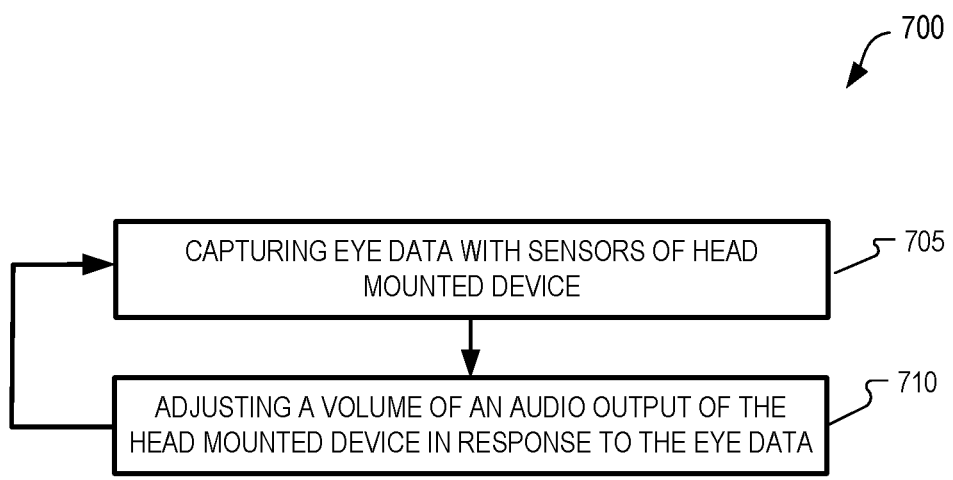
FIG. 7 illustrates a flow chart of an example method of adjusting a volume of an audio output of a head mounted device in response to eye data, in accordance with aspects of the disclosure.

FIG. 7 illustrates an example method of adjusting a volume of an audio output of a head mounted device in response to eye data, in accordance with implementations of the disclosure. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel. In some implementations, processing logic 470 executes all or a portion of process 700.

In process block 705, eye data is captured with one or more sensors of a head mounted device. The one or more sensors are configured to sense the eyebox region. The sensors may include one or more photodiodes, image sensors, or any other suitable sensor to capture eye data. As described previously, the eye data may include images of an eyebox region, for example. The eye data may include positions of various features of an ocular area of a user in the eyebox region. Eye data may include at least one of a pupil size of an eye, speed of pupil dilation of the eye, a gaze direction of the eye, or eye-movement data, for example. The eye data may include a number of saccades in a time period.

In process block 710, a volume of an audio output of the head mounted device is adjusted in response to the eye data. Adjusting the volume of the audio output may include adjusting a sound magnitude of speakers of the head mounted device where the speakers are oriented to provide sound to ears of a user of the head mounted device.

In an implementation, process 700 further includes initiating an ambient noise measurement with a microphone of the head mounted device. In this implementation, adjusting the volume of the audio output of the head mounted device is in response to the eye data and to the ambient noise measurement.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The term "processing logic" (e.g. 470) in this disclosure may include one or more processors, microprocessors, multi-core processors, Application-specific integrated circuits (ASIC), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

Network may include any network or network system such as, but not limited to, the following: a peer-to-peer network; a Local Area Network (LAN); a Wide Area Network (WAN); a public network, such as the Internet; a private network; a cellular network; a wireless network; a wired network; a wireless and wired combination network; and a satellite network.

Communication channels may include or be routed through one or more wired or wireless communication utilizing IEEE 802.11 protocols, BlueTooth, SPI (Serial Peripheral Interface), I2C (Inter-Integrated Circuit), USB (Universal Serial Port), CAN (Controller Area Network), cellular data protocols (e.g. 3G, 4G, LTE, 5G), optical communication networks, Internet Service Providers (ISPs), a peer-to-peer network, a Local Area Network (LAN), a Wide Area Network (WAN), a public network (e.g. "the Internet"), a private network, a satellite network, or otherwise.

A computing device may include a desktop computer, a laptop computer, a tablet, a phablet, a smartphone, a feature phone, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of operating a head mounted device, the method comprising:
   capturing eye data with one or more sensors of the head mounted device, wherein the one or more sensors are configured to sense an eyebox region;
   initiating an ambient light measurement with a photodetector of the head mounted device; and
   adjusting a transparency of a lens the head mounted device in response to the eye data and the ambient light measurement, wherein adjusting the transparency of the lens of the head mounted device in response to the eye data and the ambient light measurement includes:
      associating the eye data and the ambient light measurement to previous eye data paired with a previous ambient light measurement; and
      adjusting the transparency of the lens to a previously selected lens transparency selected by a user, wherein the previously selected lens transparency corresponds to the previous eye data paired with the previous ambient light measurement, and wherein the previous eye data and the previous ambient light measurement were captured by the head mounted device during a same time period.

2. The method of claim 1, wherein the eye data includes at least one of a pupil size of an eye, speed of pupil dilation of the eye, a gaze direction of the eye, or eye-movement data.

3. The method of claim 1, wherein the eye data includes one or more images of an eye.

4. The method of claim 3 further comprising:
   performing image processing on the one or more images of the eye to determine a heart rate of a user of the head mounted device, wherein adjusting the transparency of the lens is based at least in part on the heart rate of the user.

5. The method of claim 3 further comprising:
   performing image processing on the one or more images of the eye to determine at least one of movement of eyebrows, movement of eyelids, or facial muscle micro gestures, and wherein adjusting the transparency of the lens is based at least in part on the movement of eyebrows, the movement of eyelids, or the facial muscle micro gestures.

6. A method of operating a head mounted device, the method comprising:
   capturing eye data with one or more sensors of the head mounted device, wherein the one or more sensors are configured to sense an eyebox region;
   initiating an ambient light measurement with a photodetector of the head mounted device; and
   adjusting a brightness of a display of the head mounted device in response to the eye data and the ambient light measurement, wherein adjusting the brightness of the display in response to the eye data and the ambient light measurement includes:
      associating the eye data and the ambient light measurement with previous eye data paired with a previous ambient light measurement; and
      adjusting the brightness of the display to a previously selected display brightness selected by a user, wherein the previously selected display brightness corresponds to the previous eye data paired with the previous ambient light measurement, and wherein the previous eye data and the previous ambient light measurement were captured by the head mounted device during a same time period.

7. The method of claim 6, wherein the eye data includes at least one of a pupil size of an eye, speed of pupil dilation of the eye, a gaze direction of the eye, or eye-movement data.

8. The method of claim 6, wherein the eye data includes one or more images of an eye.

9. The method of claim 8 further comprising:
performing image processing on the one or more images of the eye to determine a heart rate of a user of the head mounted device, wherein adjusting the brightness of the display is based at least in part on the heart rate of the user.

10. The method of claim 8 further comprising:
performing image processing on the one or more images of the eye to determine at least one of movement of eyebrows, movement of eyelids, or facial muscle micro gestures, and wherein adjusting the brightness of the display is based at least in part on the at least one of movement of eyebrows, movement of eyelids, or the facial muscle micro gestures.

11. A method of operating a head mounted device, the method comprising:
capturing eye data with one or more sensors of the head mounted device, wherein the one or more sensors are configured to sense an eyebox region;
initiating an ambient noise measurement with a microphone of the head mounted device; and
adjusting a volume of an audio output of the head mounted device, wherein adjusting the volume of the audio output of the head mounted device is in response to the eye data and the ambient noise measurement.

12. The method of claim 11, wherein the eye data includes at least one of a pupil size of an eye, speed of pupil dilation of the eye, a gaze direction of the eye, or eye-movement data.

13. The method of claim 11, wherein the eye data includes a number of saccades in a time period.

14. The method of claim 11, wherein the eye data includes one or more images of an eye.

15. A method of operating a head mounted device, the method comprising:
capturing eye data with one or more sensors of the head mounted device, wherein the one or more sensors are configured to sense an eyebox region; and
adjusting a volume of an audio output of the head mounted device in response to the eye data, wherein adjusting the volume of the audio output includes adjusting a sound magnitude of speakers of the head mounted device that are oriented to provide sound to ears of a user of the head mounted device.

16. The method of claim 15, wherein the eye data includes at least one of a pupil size of an eye, speed of pupil dilation of the eye, a gaze direction of the eye, or eye-movement data.

17. The method of claim 15, wherein the eye data includes a number of saccades in a time period.

18. The method of claim 15, wherein the eye data includes one or more images of an eye.

* * * * *